United States Patent [19]

Hreschak et al.

[11] Patent Number: 4,498,587
[45] Date of Patent: Feb. 12, 1985

[54] APPARATUS FOR THE CONTROL OF LARVAE OF THE GYPSY MOTH AND OTHER HARDWOOD DEFOLIATORS

[76] Inventors: Bohdan O. Hreschak; Christine Hreschak, both of 55 Cecelia Dr., Wayne, N.J. 07470

[21] Appl. No.: 592,952

[22] Filed: Mar. 23, 1984

Related U.S. Application Data

[63] Continuation-in-part of Ser. No. 356,738, Mar. 10, 1982, Pat. No. 4,447,447.

[51] Int. Cl.$^3$ .................... A01N 43/08; B65D 85/00; B65D 85/72
[52] U.S. Cl. .................... 206/525; 206/384; 222/327; 514/919; 514/473
[58] Field of Search ................ 206/525, 384; 222/327; 424/285, DIG. 10

[56] References Cited

U.S. PATENT DOCUMENTS

| | | | |
|---|---|---|---|
| 3,775,483 | 11/1973 | Frederickson et al. | 424/DIG. 10 |
| 3,818,102 | 6/1974 | Partos | 424/285 |
| 4,193,986 | 3/1980 | Cox | 424/DIG. 10 |
| 4,374,851 | 2/1983 | Hunt et al. | 424/285 |

Primary Examiner—Allen J. Robinson
Attorney, Agent, or Firm—Bucknam and Archer

[57] ABSTRACT

A cartridge is described which is packed with a composition which comprises a mixture of at least one aliphatic aldehyde in the range of two to seven carbon atoms ($C_2$–$C_7$), at least one sulfide or disulfide, ranging from one to fourteen carbon atoms ($C_1$–$C_{14}$), at least one carboxylic acid, ranging from 4 to 6 carbons atoms, in an appropriate carrier. The use of at least one diketofuran of 5 to 7 carbon atoms is optional. The cartridge is provided with a dispensing nozzle to apply the composition to a tree trunk in the form of a closed band. When so applied, it prevents Gypsy Moth larvae and other hardwood defoliators to ascend the tree and thus interrupts the feeding cycle of these defoliators.

12 Claims, No Drawings

APPARATUS FOR THE CONTROL OF LARVAE OF THE GYPSY MOTH AND OTHER HARDWOOD DEFOLIATORS

This application is a continuation-in-part of U.S. Ser. No. 356,738 filed Mar. 10, 1982, now U.S. Pat. No. 4,447,447.

The present invention relates to larvae or caterpillars of Gypsy Moth and other hardwood defoliators such as Linden Looper, Forrest Tent Caterpillar and Elm Spanworm. More specifically, the invention relates to the device and specifically cartridges for the application of novel compositions useful for preventing the larvae from climbing up trees, feeding upon the foliage of the trees, pupate on the trees where they rested during last larval stages. Thus, the invention is intended to interrupt the normal life cycle of these defoliators.

In the life cycle of Gypsy Moth, there are four stages—egg, larva (caterpillar), pupa (cocoon) and moth. Gypsy Moth has one generation a year, overwintering in egg masses, which it attaches either to the tree or outside the tree on such objects as rocks, stumps, walls, ground foliage, logs, fences, houses, wood piles and in general any outdoor object where it finds protective cover. Eggs are hatched in late April or early May. Egg hatching may continue over a period of 2 to 3 weeks, depending on the location of egg masses and exposure to sunlight. The caterpillar phase of Gypsy Moth is composed of 5–6 molting stages and the number of days involved in each stage varies from four to ten days, depending on weather, temperature and sunlight conditions. During the first, second and third stage, the larvae which hatched high on tree trunks stay on tree crowns. When caterpillar molts to the fourth stage, it enters the most destructive phase of its life, and its behaviour changes dramatically. During this phase larvae feed voraciously at night and then descend to the ground at dawn by the production of "silk" webs. The larvae rest during the day in leaf litter, at the base of trees, among rocks or any protected location on the ground they feel safe. At dusk, the larvae crawl up the trunk of trees to feed again on the leaves and thus, the process of defoliation continues. It is theorized, that this movement up and down the tree is triggered by low light (U.S. Department of Agriculture, Home and Garden Bulletin No. 235), but it is also known, that larvae descend to the ground in search of moisture, for instance, morning dew and cooler temperature on the ground.

More specifically, the present invention is directed to preventing the first stage larvae, which winter-nested and spring-hatched off the tree, from ascending the trees and preventing the fourth and fifth stage adult larvae, which at dawn descended to the ground in search of moisture and rest, from re-entering the trees at dusk.

The known methods of controlling the spread and infestation of gypsy moth and other defoliators, used by state, federal and local governments, involve the use of sex attractants, pesticides, microbial insecticides and parasites. For example, the well publicized, synthetically produced hormone Pheromone is supposed to imitate the scent of the female moth, with the latter seducing the male moth into the death trap and thus disrupting the mating of the moths. This hormone is a valuable and effective tool for the detection and evaluation of populations of the insects but its use as a control of Gypsy Moth infestation is limited and still under investigation (U.S. Department of Agriculture, Plant Protection and Quarantine Programs, Bulletin No. 1006). The most widely used method for controlling the spread of Gypsy Moth is still the chemical pesticide known under the trade name Sevin, which is applied to trees, under high pressure, in the form of a very fine mist. This pesticide, however, is extremely toxic to animals, birds, humans and indeed, it has been reported to cause birth defects and to kill beneficial insects.

Thus, in spite of all the efforts to contain Gypsy Moth infestation, today, this pest has spread to all six New England states, as well as New Jersey, New York, Pennsylvania, Maryland, Delaware and even portions of Central Michigan, reaching epidemic proportions (U.S. Department of Agriculture, Animal and Plant Health Service Bulletin No. 1006).

One object of this invention is to provide a device for the application of a novel composition of matter, which creates a barrier and which prevents Gypsy Moth larvae and other hardwood defoliators from ascending trees and feeding on its foliage.

It is another object of this invention to provide a safe, non-toxic control to Gypsy Moth infestation, which poses no hazard to humans and all living matter in the environment, such as birds, animals and beneficial insects.

It is a further object of this invention to provide a barrier, which will withstand most climatic conditions i.e. rain, sunlight, heat, strong winds, snow, frost, thus eliminating constant reapplication of the composition to trees.

It is still another object of this invention to provide a device for the application of novel composition to trees easily and economically.

The crux of the present invention resides in a device, specifically a cartridge for the application of a combination of certain ingredients in specified proportions which produces a "barrier", that is, which stops the Gypsy Moth caterpillars and other defoliators from crossing it. Thus, this invention is based on a totally new concept of controlling spread of the pests because it deprives the caterpillar of food.

In accordance with the present invention, the cartridge contains a composition comprising a mixture of:

(a) at least one member from the group of aliphatic aldehydes, having 2–7 carbon atoms;

(b) at lest one member from the group of organic sulfides and disulfides with carbon atoms ranging from 1 to 14;

(c) at least one member from the group of carboxylic acids with carbon atoms ranging from 1 to 14.

The mixture is incorporated in a suitable carrier and a solvent is preferably used. The mixture, when applied around the tree trunk in the form of a band of width between ⅛ and 3 inches, prevents the larvae from crossing it.

(d) an optional ingredient is a member selected from the group of diketo furans.

The solvent may be, for instance, soybean oil, benzyl alcohol or a mixture of soybean oil with benzyl alcohol, in the proportion of 1–2 parts of soybean oil to 2–1 parts of benzyl alcohol.

In accordance with a preferred embodiment of the invention, the composition of matter, as described hereinabove, is mixed with petroleum jelly (vaseline) as a carrier and is packed in a cartridge. A synthetic oil may be used, instead of vaseline or petroleum oil, appropriately thickened with a soap, such as the soaps of aluminum, barium, calcium, lithium, sodium and strontium.

Several conventional types of cartridges may be used, such as the cartridges made of plastic materials, manufactured by Voplex of Rochester, N.Y. These cartridges are provided with a plunger, which is used to seal the cartridge after it has been filled. The cartridge may be packed by hand or by filling machines. At the time when the material is to be discharged from the nozzle, a convenient way involves the use of a caulking gun. The cartridge is placed into the caulking gun. The nozzle is cut by a knife and the trigger of the caulking gun is pressed so that the piston of the caulking gun presses against the plunger of the cartridge and the material is discharged through the nozzle. The nozzle is cut at the desired height so that one may apply a band of the desired thickness.

It has been found that the novel composition in the cartridge, according to the present invention, when applied to tree trunks, maintains its effectiveness throughout the year, because it withstands climatic conditions of sunlight, rain, heat, strong winds, snow, sleet and frost, without essentially losing its inherent barrier properties the following year. Thus, it is sufficient to apply the composition to the trees once every two years in order to control the pest infestation.

In a study conducted over a period of 36 months, it has been conclusively established that the novel composition acts as a barrier resulting in a dramatic decrease in tree defoliation. This was evidenced by great masses of larvae gathered under the applied bands, unable to reach the branches with leaves, their next feeding station, so that they shriveled up and died. Thus, the present invention affords considerable advantage to the home owner, tree grower, nursery owner, because it provides a simple and inexpensive method of reducing defoliation and permanent damage to the tree.

A very satisfactory composition, in accordance with this instant invention, comprises 0.05–10.0 parts of at least one aliphatic aldehyde with carbon atoms ranging from 2 to 7, preferably iso-butyraldehyde, 0.05–10.0 parts of at least one sulfur compound with carbon atoms ranging from 1 to 14, preferably di-butyl disulfide, 0.05–10.0 parts of at least one diketofuran, specifically 2-methyl-4-hydroxy 3-(2H)-furanone, 2,5,-dimethyl-4-hydroxy 3-(2H)-furanone, also known as Furaneol, 2-ethyl-5-methyl-4-hydroxy 3-(2H)-furanone, 0.10–20.0 parts of at least one carboxylic acid with carbon atoms ranging from 1 to 14, preferably iso-butyric acid and 50–99.75 parts of carrier-bulker material in the form of petroleum jelly. Iso-Valeraldehyde may be used in partial replacement of iso-butyraldehyde, up to 0.025–5.0 parts of iso-valeraldehyde in combination with about 0.025–5.0 parts of iso-butyraldehyde. Dimethyl disulfide may be used in partial replacement of dibutyl disulfide, up to 0.025–5.0 parts of dimethyl sulfide in combination with about 0.025–5.0 parts of dibutyl disulfide. n-Caproic acid may be used in partial replacement of iso-butyric acid, up to 0.05–10.0 parts of n-caproic acid in combination with 0.05–10.0 parts of iso-butyric acid.

It is possible to use all the three diketofurans mentioned hereinabove in an amount each not in excess of 33% of the total amount of the diketofurans and it is also possible to eliminate the diketofurans.

It is preferable to use a solvent in the amount of 0.125 parts up to 50 parts of solvent, preferably 0.25 parts per 0.25 parts of the mixture, not including carrier or bulking agent.

Although it is possible to mix all the ingredients together, it is preferable to add the solvent to the ingredients before they are incorporated into the carrier, if a solvent is used, and blend the mixture under high speed agitation. The mixture is then added to the carrier, which has been previously heated to a soft semi-liquid state. The final composition is then blended under mechanical mixing, for a period of time between 1 and 10 minutes, depending upon the size of the mixing unit, the amount of material used and the speed of mixing. Partial cooling of the composition might be required, depending upon the type of material the packing cartridge is made of. If the cartridge is of the spiral type, with a metal lining, it is not necessary to cool the composition for packing. If, however, one of the plastic type cartridges is used, the temperature of the material may be lowered before it is packed.

For the purpose of illustration of the invention, the following example is described in detail hereinbelow, but the invention is not to be considered as limited to the particular ingredients and the proportions given therein.

EXAMPLE 1

In a vessel of 1 gallon capacity, equipped with an electrical wrap-around heating tape and a high speed mixer, were placed 0.25 pound of refined soybean oil, 0.25 pounds of benzyl alcohol, 0.20 pound of iso-butyric acid, 0.1 pound of 2,5-dimethyl 4-hydroxy 3 (2H)-furanone, 0.1 pound of di-butyl disulfide and 0.1 pound of iso-butyraldehyde. The ingredients were blended by mixing 5 minutes with a high speed mixer at 100 revolutions per minute. The heating tape kept the mixture at 155°–165° F.

In another vessel of 50 gallon capacity, equipped with an outer jacket for heating or cooling purposes, 199 pounds of petroleum jelly was heated under constant agitation at 35 revolutions per minute, until it reached a soft semi-liquid state.

Then the mixture from the 1 gallon vessel was transferred to the 50 gallon vessel. Mixing was continued for another 10 minutes at 50 revolutions per minute, until the composition became homogeneous.

A similar composition was prepared from 0.05 pounds dimethyl sulfide and 0.05 pounds dibutyl disulfide, and the same amounts of the diketofuran and iso-butyric acid, soybean oil and benzyl alcohol, without affecting the essential properties of the finished product.

Following the mixing step, the mixture was cooled to room temperature by passing 65° F. water through the outer jacket of the vessel. The finished product was transferred to a standard 5 gallon capacity bucket equipped with a caulking cartridge loader. The material was packed by means of this loader into cartridges of 11 ounces capacity, equipped with a discharging nozzle. The use of the "caulking tube type cartridge" has been found to be an easy, practical and economical method for the application of the composition to trees, because the composition is discharged by means of a caulking gun. The novel composition packed in this conventional cartridge was applied in the form of a bead, about $\frac{3}{8}$–$\frac{1}{2}$ inches in diameter, allowing tight filling of all crevices and irregularities in the bark surface.

EXAMPLE 2

The same ingredients in the same proportions as described in Example 1 were used and the same procedure was followed except that 2,5-dimethyl 4-hydroxy 3(2H)-furanone was omitted. The composition after cooling to room temperature was packed into cartridges of the same type and size as used in Example 1.

What is claimed is:

1. A cartridge containing a composition effective to prevent gypsy moth caterpillars and other hardwood defoliators from ascending trees and devouring their foliage, said cartridge being packed with a composition comprising a mixture of (a) 0.05–10.0 parts of at least one aliphatic aldehyde with 2–7 carbon atoms, (b) 0.05–10.0 parts of at least one sulfur compound which is dibutyl disulfide, or a mixture of dibutyl disulfide and dimethyl sulfide, (c) 0–10.0 parts of at least one diketofuran with carbon atoms ranging from 5 to 7, (d) 0.10–20 parts of at least one carboxylic acid with 4–6 carbon atoms, (e) a solvent in the amount of 0–50 parts and (f) 50–99.5 parts of a bulking agent.

2. The cartridge according to claim 1 wherein the composition comprises a solvent which is soybean oil or benzyl alcohol or a mixture thereof in the ratio of 1–2 parts of soybean oil to 2–1 parts of benzyl alcohol, and the solvent is in an amount of between 0.25 and 50 parts.

3. The cartridge according to claim 1, wherein in said composition the aliphatic aldehyde is iso-butyraldehyde.

4. The cartridge according to claim 1 wherein in said composition, the diketofuran is (a) 2-methyl-4-hydroxy 3-(2H)-furanone; (b) 2,5-dimethyl-4-hydroxy 3-(2H)-furanone or (c) 2-ethyl-5-methyl-4-hydroxy 3-(2H)-furanone or a mixture thereof in the total amount of 0.1 part.

5. The cartridge according to claim 4, wherein in said composition said diketofuran is (a) 2-methyl-4-hydroxy 3-(2H)-furanone; (b) 2,5-dimethyl-4-hydroxy 3-(2H)-furanone and (c) 2-ethyl-5-methyl-4 hydroxy 3-(2H)-furanone in essentially equal amounts.

6. The cartridge according to claim 1 wherein in said composition the carboxylic acid is iso-butyric acid.

7. The cartridge according to claim 1 wherein in said composition the bulking agent is petroleum jelly.

8. The cartridge according to claim 1, wherein in said composition the bulking agent is synthetic oil or petroleum oil thickened with a soap.

9. The cartridge according to claim 1 wherein said composition comprises iso-butyraldehyde and iso-valeraldehyde in amount of 0.025–5.0 parts of isovaleraldehyde to 0.025–5.0 parts of iso-butyraldehyde.

10. The cartridge according to claim 1 wherein said composition comprises dibutyl disulfide and dimethyl disulfide, in amount of 0.025–5.0 parts of dimethyl disulfide to 0.025–5.0 parts of dibutyl disulfide.

11. The cartridge according to claim 1 wherein said composition comprises iso-butyric acid and n-caproic acid, in amount of 0.05–10.0 parts of n-caproic acid to 0.05–10.0 parts of iso-butyric acid.

12. The cartridge according to claim 1 wherein in said composition the bulking agent is petroleum oil thickened with a soap of aluminum, barium, calcium, lithium, sodium or strontium.

* * * * *